(12) United States Patent
Laroya et al.

(10) Patent No.: US 8,002,815 B2
(45) Date of Patent: Aug. 23, 2011

(54) DELIVERY SYSTEM AND METHOD FOR VASCULAR PROSTHESIS

(75) Inventors: Gilbert S. Laroya, Santa Clara, CA (US); Gerald Ray Martin, Redwood City, CA (US); Rainier Betelia, San Jose, CA (US); Edward A. Estrada, Menlo Park, CA (US)

(73) Assignee: NovoStent Corporation, Mountain View, CA (US)

( * ) Notice: Subject to any disclaimer, the term of this patent is extended or adjusted under 35 U.S.C. 154(b) by 1185 days.

(21) Appl. No.: 11/716,478

(22) Filed: Mar. 9, 2007

(65) Prior Publication Data

US 2008/0221657 A1    Sep. 11, 2008

(51) Int. Cl.
A61F 2/06    (2006.01)

(52) U.S. Cl. ...................................... 623/1.12

(58) Field of Classification Search ............... 623/1.11, 623/1.12, 1.22, 1.53; 606/108, 198, 200
See application file for complete search history.

(56) References Cited

U.S. PATENT DOCUMENTS

| | | | |
|---|---|---|---|
| 4,553,545 A | 11/1985 | Maass et al. | |
| 4,800,882 A | 1/1989 | Gianturco | |
| 4,969,458 A | 11/1990 | Wiktor | |
| 5,603,722 A | 2/1997 | Phan et al. | |
| 5,632,771 A * | 5/1997 | Boatman et al. | 623/1.15 |
| 5,772,668 A * | 6/1998 | Summers et al. | 623/1.11 |
| 5,797,952 A | 8/1998 | Klein | |
| 5,865,723 A | 2/1999 | Love | |
| 6,027,516 A * | 2/2000 | Kolobow et al. | 623/1.11 |
| 6,425,915 B1 | 7/2002 | Khosravi et al. | |
| 6,514,285 B1 * | 2/2003 | Pinchasik | 623/1.22 |
| 6,562,064 B1 | 5/2003 | deBeer | |
| 6,572,648 B1 | 6/2003 | Klumb et al. | |
| 6,607,551 B1 | 8/2003 | Sullivan et al. | |
| 6,645,237 B2 | 11/2003 | Klumb et al. | |
| 2001/0005793 A1 * | 6/2001 | Brenneman | 623/1.11 |
| 2002/0004679 A1 * | 1/2002 | Eury et al. | 623/1.15 |
| 2002/0151956 A1 | 10/2002 | Chobotov et al. | |
| 2004/0122504 A1 | 6/2004 | Hogendijk | |
| 2004/0186556 A1 | 9/2004 | Hogendijk et al. | |
| 2004/0186557 A1 | 9/2004 | Gambale et al. | |

(Continued)

FOREIGN PATENT DOCUMENTS

WO    WO 00/62711    10/2000

OTHER PUBLICATIONS

International Search Report dated Aug. 22, 2008 from corresponding International App. No. PCT/US 08/56079.

*Primary Examiner* — Anhtuan T Nguyen
*Assistant Examiner* — David Eastwood
(74) *Attorney, Agent, or Firm* — James F. Hann; Haynes Beffel & Wolfeld LLP

(57) ABSTRACT

A delivery system for an implantable vascular prosthesis is provided for a vascular prosthesis including at least first and second helical sections having alternating directions of rotation that are coupled to one another at apices. The delivery system includes an elongate body, a plurality of retainers and an outer sheath. The plurality of retainers are configured to temporarily retain a plurality of inner wound apices of the vascular prosthesis. The outer sheath is configured to retain the vascular prosthesis in a contracted state on the elongate body.

10 Claims, 17 Drawing Sheets

U.S. PATENT DOCUMENTS

| | | |
|---|---|---|
| 2005/0149164 A1* | 7/2005 | Rivelli ............... 623/1.11 |
| 2005/0165469 A1 | 7/2005 | Hogendijk |
| 2006/0079955 A1* | 4/2006 | Brown ............... 623/1.22 |
| 2006/0136033 A1 | 6/2006 | Hermann et al. |
| 2006/0136035 A1 | 6/2006 | Hermann et al. |
| 2007/0129786 A1 | 6/2007 | Beach et al. |
| 2007/0185560 A1* | 8/2007 | Roeder et al. ............ 623/1.15 |
| 2007/0208416 A1 | 9/2007 | Burpee et al. |
| 2008/0125849 A1 | 5/2008 | Burpee et al. |

* cited by examiner

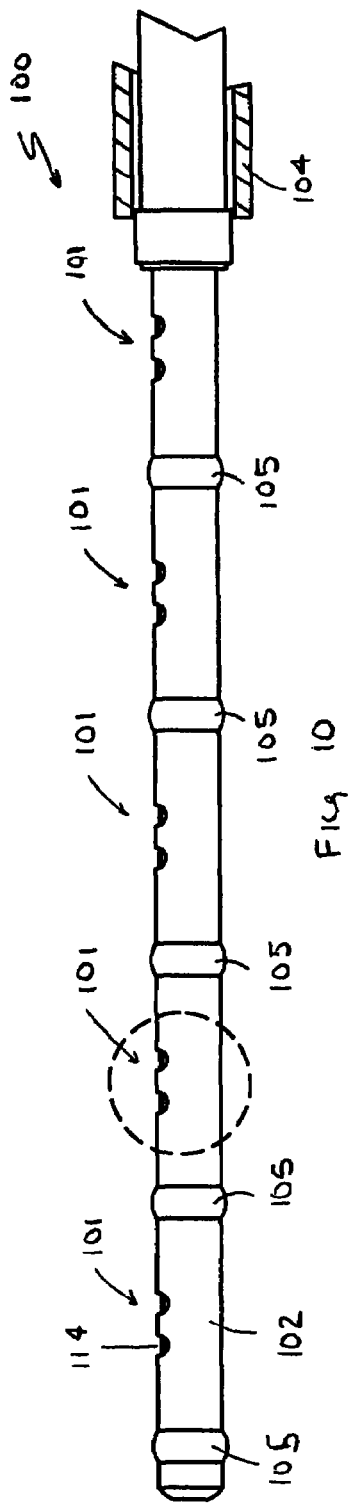
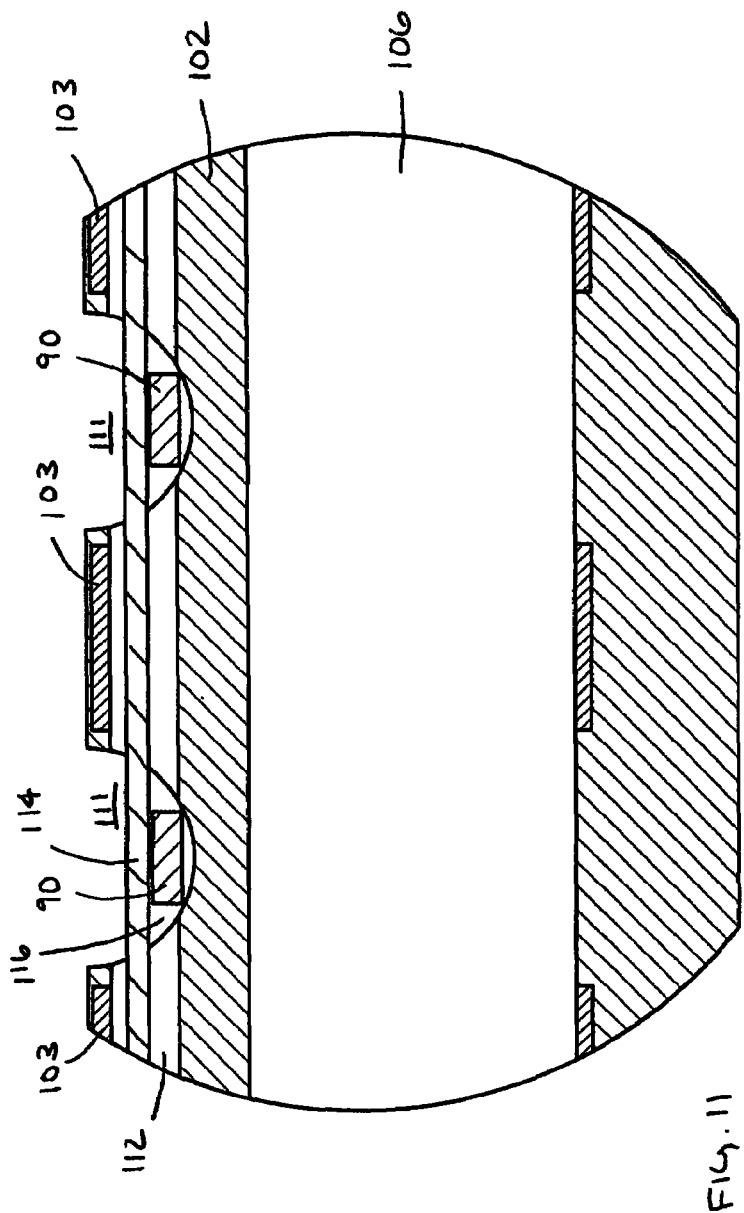
Fig. 10
Fig. 11

DELIVERY SYSTEM AND METHOD FOR VASCULAR PROSTHESIS

FIELD OF THE INVENTION

The present invention relates to a delivery system for an implantable vascular prosthesis configured for use in a wide range of applications, and more specifically, to a delivery system for a prosthesis having an alternating helical section.

BACKGROUND OF THE INVENTION

Today there are a wide range of intravascular prostheses on the market for use in the treatment of aneurysms, stenoses, and other vascular irregularities. Balloon expandable and self-expanding stents are well known for restoring patency in a stenosed vessel, e.g., after an angioplasty procedure, and the use of coils and stents are known techniques for treating aneurysms.

Previously-known self-expanding stents generally are retained in a contracted delivery configuration using an outer sheath or a release wire, then self-expand when the sheath or release wire is retracted. Such stents commonly have several drawbacks, for example, the stents may experience large length changes during expansion (referred to as "foreshortening" or "jumping") and may shift within the vessel prior to engaging the vessel wall, resulting in improper placement. Another disadvantage is that after the stent is deployed it can experience longitudinal movement within the vessel (also referred to as "migration"), which can be attributed to repetitive longitudinal loading and unloading of the stent.

Additionally, repetitive loading and unloading of a stent have also been known to cause fatigue induced strut failure, which may contribute to restenosis and subsequent vessel narrowing and/or occlusion. Additionally, many self-expanding stents have relatively large delivery profiles because the configuration of their struts limits further compression of the stent. Accordingly, such stents may not be suitable for use in smaller vessels, such as cerebral vessels and coronary arteries.

For example, PCT Publication WO 00/62711 to Rivelli describes a stent comprising a helical mesh coil having a plurality of turns and including a lattice having a multiplicity of pores. The lattice is tapered along its length. In operation, the plurality of turns are wound into a reduced diameter helical shape, and then constrained within a delivery sheath. The delivery sheath is retracted to expose the distal portion of the stent and anchor the distal end of the stent. As the delivery sheath is further retracted, subsequent individual turns of the stent unwind to conform to the diameter of the vessel wall.

The stent described in the foregoing publication has several drawbacks. For example, due to friction between the turns and the sheath, the individual turns of the stent may "bunch up," or overlap with one another, when the delivery sheath is retracted. In addition, once the sheath is fully retracted, the turns may shift within the vessel prior to engaging the vessel wall, resulting in improper placement of the stent. Moreover, because the distal portion of the stent may provide insufficient engagement with the vessel wall during subsequent retraction of the remainder of the sheath, ambiguity concerning accuracy of the stent placement may arise.

In another example, U.S. Pat. No. 5,603,722 to Phan et al. describes a stent formed of expandable strip-like segments. The strip-like segments are joined along side regions in a ladder-like fashion along offsetting side regions. A shortcoming of such a stent is that the junctions between adjacent segments are not provided with a means of addressing longitudinal loading. As a result, such a stent is susceptible to strut fracture.

In another example, U.S. Pat. No. 6,607,551 to Sullivan et al. describes a stent delivery system that includes a nested stabilizer. The nested stabilizer is constructed to engage the stent inner periphery with a high-friction sleeve or coating or a plurality of protuberances. The stabilizer enables transfer of longitudinal force to the stent without collapsing a low-column-strength of the stent. The device however does not provide any mechanism for loading a stent having an alternating helical configuration.

In view of the drawbacks of previously known devices, it would be desirable to provide a delivery system for an implantable vascular prosthesis comprising a plurality of helical portions joined together, wherein the prosthesis is configured to be used in a wide range of applications including maintaining patency in a vessel and delivering drugs to a vessel.

It further would be desirable to provide a delivery system for a vascular prosthesis having one or more radially expanding anchors that allow for additional control over the deployment of the vascular prosthesis at a desired location within a vessel.

SUMMARY OF THE INVENTION

In view of the foregoing, it is an object of the present invention to provide apparatus and methods for delivering an implantable vascular prosthesis comprising a plurality of helical stent portions having alternating directions of rotation joined together, wherein the prosthesis is configured to be used in a wide range of applications including, but not limited to, maintaining patency in a vessel and delivering drugs to a vessel.

It is another object of the present invention to provide apparatus and methods for delivering a vascular prosthesis having at least one alternating helical section wherein the apparatus and method allow for controlled deployment of the vascular prosthesis at a desired location within a vessel.

These and other objects of the present invention are accomplished by providing an apparatus for delivering a vascular prosthesis comprising a plurality of helical portions having alternating directions of rotation that are joined together at apices. The device is configured to temporarily retain a plurality of apices during loading. The device may also be used to retain the prosthesis until deployment.

In a preferred embodiment, the delivery system includes an elongate body and an outer sheath. The elongate body includes a plurality of recesses configured to be engaged by alternating apices of an alternating helical section of a vascular prosthesis. A retaining wire extends through a lumen in the elongate body that intersects the recesses so that the wire extends across the recesses. The outer sheath is configured so that it receives a portion of the elongate body and a vascular prosthesis loaded on the elongate body that is in a contracted state.

The delivery system further may comprise stops that prevent axial movement of a vascular prosthesis relative to the elongate body. Additional stops may be included that prevent relative motion between one or more radially expandable anchor sections and the elongate body.

The delivery system of the present invention is used to load a vascular prosthesis and to deliver it to a target vessel in a contracted state, constrained within the outer sheath. In the contracted state, the helical section is wound down to a reduced diameter configuration, so that adjacent turns preferably partially overlap and so that the apices are located either radially outward or radially inward with respect to each helical portion.

In a preferred method of operation of a prosthesis delivery system, an alternating helical section of the prosthesis is provided in its contracted state within an outer sheath and the prosthesis is fluoroscopically advanced into a selected vessel using techniques that are known in the art. The alternating helical section then is positioned adjacent a target region of a vessel, such as a stenosed region. The outer sheath then is retracted proximally to cause the first helical portion of the alternating helical section to self-deploy and engage the vessel wall at the target region. Advantageously, by overlapping portions of the alternating helical section, the alternating helical section will unroll in a controlled manner. This technique ensures that the prosthesis will not shift within the vessel during deployment.

Methods of using the delivery system of the present invention, for example, in the treatment of the peripheral vasculature, also are provided.

BRIEF DESCRIPTION OF THE DRAWINGS

Further features of the invention, its nature and various advantages will be more apparent from the accompanying drawings and the following detailed description of the preferred embodiments, in which:

FIG. 10 is a side view of a delivery device configured for delivering the vascular prosthesis of FIG. 9;

FIG. 11 is a cross-sectional view of a portion of the delivery device of FIG. 10;

DETAILED DESCRIPTION OF THE INVENTION

The delivery system, according to the present invention, is configured to deliver a vascular prosthesis having an alternating helix configuration that provides a substantially smaller delivery profile than previously known devices. Additionally, the delivery device is configured to load such that apices located radially inward on the vascular prosthesis may be temporarily coupled to allow proper loading of the prosthesis.

Figure 1:
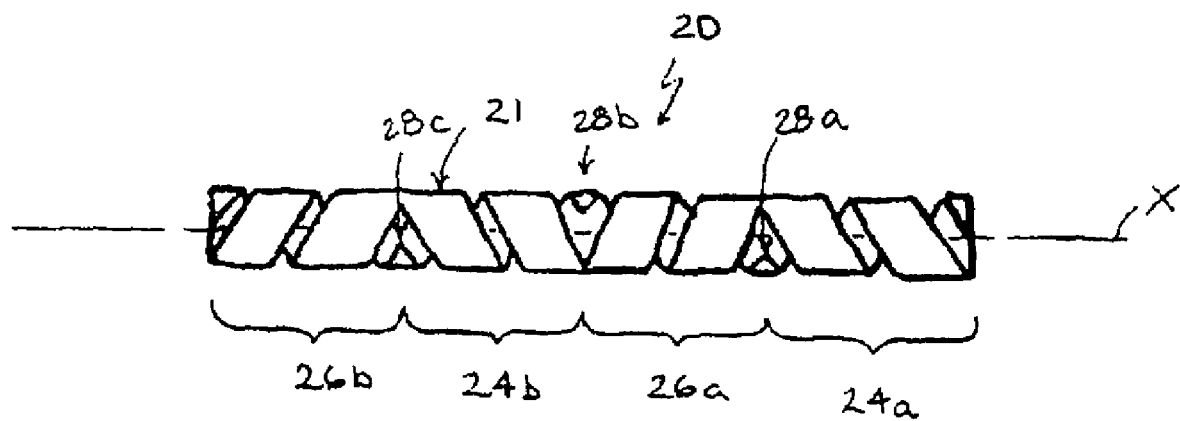
FIG. 1 is a schematic representation of a vascular prosthesis of the present invention in a deployed state.
Figure 2:
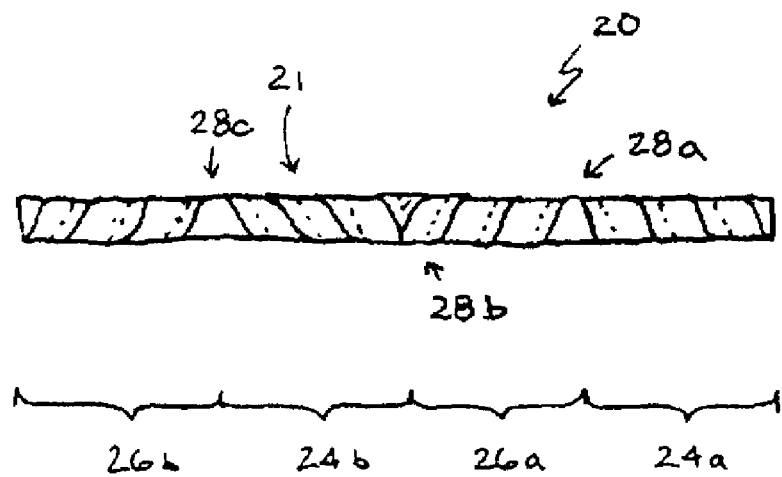
FIG. 2 is a schematic representation of the vascular prosthesis of the present invention in a contracted state.

Referring now to FIGS. 1 and 2, a schematic representation of a vascular prosthesis constructed in accordance with principles of the present invention is described. Vascular prosthesis ("stent") 20 illustratively comprises alternating helical section 21 capable of assuming contracted and deployed states. In FIG. 1, alternating helical section 21 is depicted in the deployed state.

Alternating helical section 21 is constructed from two or more helical portions having at least one change in the direction of rotation of the helices, and being joined at apex portions where the directions of rotation of adjacent helices change. In particular, first (i.e., proximal-most) helical portion 24a has a generally clockwise rotation about longitudinal axis X of prosthesis 20. Helical portion 26a adjoins the distal end of helical portion 24a at apex 28a and has a generally counter-clockwise rotation about longitudinal axis X. Helical portion 24b adjoins the distal end of helical portion 26a at apex 28b, and in turn is coupled to the proximal end of helical portion 26b at apex 28c. As a result of the alternating direction of rotation of the adjoining helical portions 24a, 26a, 24b and 26b of vascular prosthesis 20 includes three apices 28a, 28b and 28c that are oriented such that they point in alternating directions about the circumference of vascular prosthesis 20, generally in a plane that is normal to longitudinal axis X of vascular prosthesis 20. Preferably, each helical portion includes at least one full helical turn between adjacent apices. However, each helical portion may include more or less turns between adjacent apices, for example a helical portion may include 0.5-2.0 helical turns between adjacent apices.

A significant advantage of alternating helical section 21 as compared to other vascular prosthesis structures is that apices 28 of alternating helical section 21 provide additional anchoring force at discrete locations along the length of alternating helical section 21. That anchoring force may be used to increase the radial force applied by the vascular prosthesis to a vessel wall as well as providing additional migration resistance. That anchoring force may be increased if desired by flaring out the ends and/or apices of the alternating helical section. Those portions may be flared outward by applying expansion and heat treatment so that those portions have a larger expanded diameter than the remainder of alternating helical section 21. Additionally, the alternating helical configuration also allows the wall thickness of the device to be reduced because the design provides increased radial strength.

Alternating helical section 21 preferably is formed from a solid tubular member comprised of a shape memory material, such as nickel-titanium alloy (commonly known in the art as Nitinol). However, it should be appreciated that alternating helical section 21 may be constructed from any suitable material recognized in the art. The solid tubular member then is laser cut, using techniques that are known in the art, to define a specific pattern or geometry in the deployed configuration. Preferably, alternating helical section 21 is cut from the tube so that helical portions 24a, 26a, 24b, 26b are integrally formed as a single monolithic body. However, it should be appreciated that separate helical portions may be mechanically coupled, such as by welding, soldering or installing mechanical fasteners to construct alternating helical section 21. An appropriate expansion and heat treatment then may be applied to alternating helical section 21 of vascular prosthesis 20 so that the device may be configured to self-deploy from a contracted, delivery configuration to the deployed configuration.

Referring now to FIG. 2, vascular prosthesis 20 is shown in the contracted and partially overlapped, delivery configuration, wherein alternating helical section 21 is in the contracted, reduced diameter state. Alternating helical section 21, however, is placed in the contracted state by winding helical portions 24, 26 about longitudinal axis X. When vascular prosthesis 20 is loaded onto a delivery device, apices 28a and 28c may be temporarily retained on an elongate body of a delivery system, and apex 28b and the distal and proximal ends of alternating helical section 21 are rotated relative to the elongate body until vascular prosthesis is in the contracted state as shown. As a result, apices 28a and 28c are wrapped radially inward of the remainder of vascular prosthesis 20 and will be generally referred to herein as "inner apices." Conversely, apex 28b, which will be generally referred to as an "outer apex," and the distal and proximal ends of alternating helical section 21 are wrapped radially outward of the remainder of alternating helical section 21.

Consequently, apices 28a and 28c are tightly wound onto the shaft of the delivery catheter and the remainder of each helical portion 24, 26 is wound against the shaft so that each turn of each portion 24, 26 overlaps an adjacent turn. For example, in some embodiments, approximately ⅔ of a layer is overlapped by the next layer. As a result, apex 28b and the distal and proximal ends of alternating helical section 21 are located furthest radially outward on the rolled alternating helical section 21. The overlap of the turns of helical portions 24, 26 are indicated by dashed lines in FIG. 2. The overlapping turns of alternating helical section 21 thus secure apices 28a and 28c when vascular prosthesis 20 is disposed within a delivery system. In addition, the overlapping of turns results in vascular prosthesis 20 having a unique deployment sequence that allows for increased control over its placement. Moreover, the unique configuration of alternating helical section 21 require a delivery system that allows for temporarily retaining the inner apices of alternating helical section 21 at least during loading.

Figure 3:
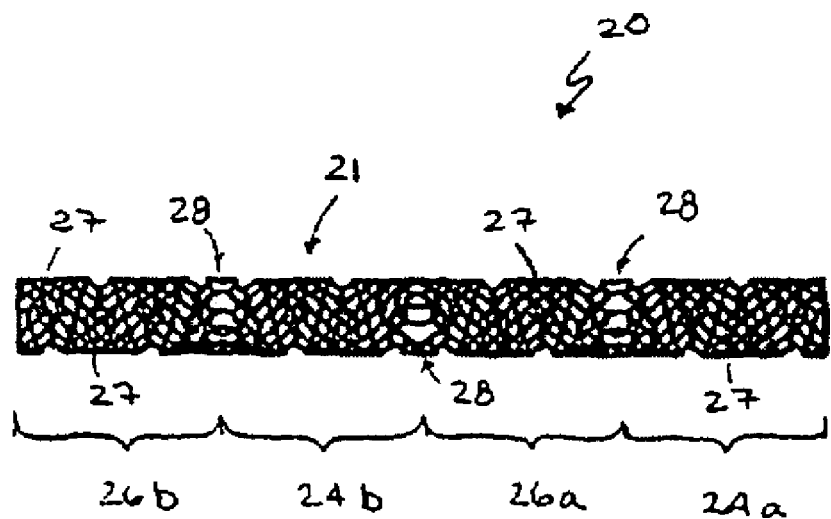
FIG. 3 is a side view of a vascular prosthesis of the present invention.
Figure 4:
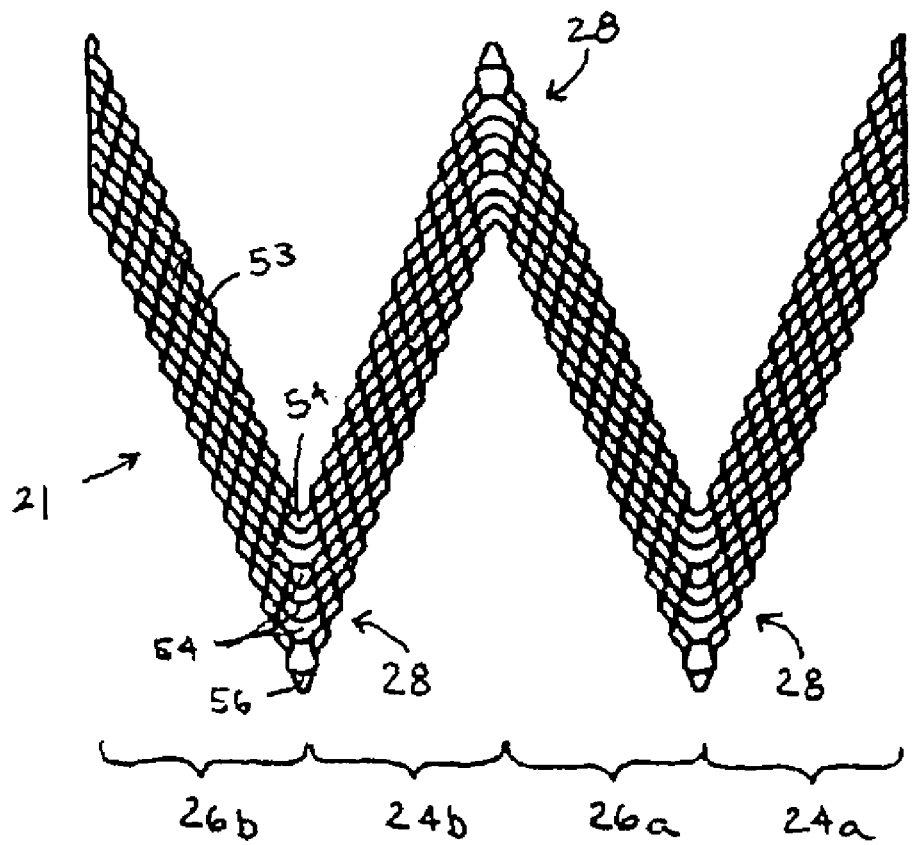
FIG. 4 is a schematic representation of the vascular prosthesis of FIG. 3 shown in a flattened configuration.

Referring now to FIGS. 3 and 4, an embodiment of vascular prosthesis 20, constructed in accordance with principles of the present invention, is described. It should be appreciated that FIG. 4 is a schematic view of vascular prosthesis 20 as it would appear if it were flattened. The components of vascular prosthesis 20 are identical to those depicted in FIGS. 1 and 2 and identical reference numbers are employed in the following description.

Alternating helical section 21 preferably comprises a helical mesh configuration including two or more helical portions 27. Helical portions 27 may include multiplicity of openings 53, 54, 56 of different shapes and sizes. The shape, size and orientation of any particular opening is selected to provide a desired response to longitudinal loads and also may be dependent upon the location of the openings within the mesh structure. The shape, size and orientation of the openings may also be selected to provide desired deployment, unwrapping, radial force and surface area coverage characteristics.

As shown in FIG. 4, alternating helical section 21 includes diamond-shaped openings 53 of generally equal size through the majority of each helical portion 24, 26.

A wide variety of openings may be employed at apices 28a, 28b and 28c, where the helical portions adjoin adjacent helical portions. The openings may have any shape and/or size desired. Some designs include diamond, polygon, circles, ellipses, elongated diamonds, etc. In addition, the openings of apices 28 need not be symmetric with respect to a centerline of apex 28. It should be appreciated that the size, shape and orientation of any of the openings may be selected so that in the deployed state some struts may bow radially outward or inward so that they interlock with adjacent, overlapping openings.

In FIG. 4, each apex includes plurality of openings 54 and one tip opening 56 that forms a tip of the respective apex, which may be triangular as shown. Openings 54 are defined by struts 55 that extend between adjacent helical portions 24, 26.

Figure 5:
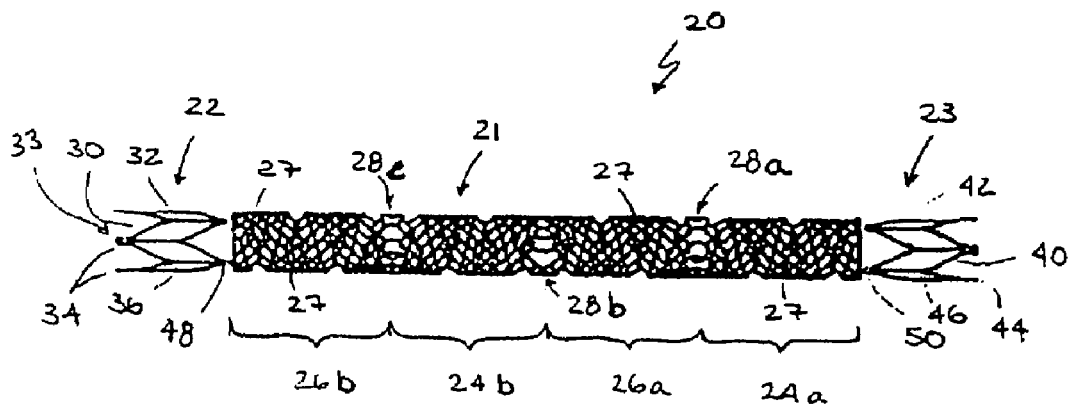
FIG. 5 is a side view of a vascular prosthesis of the present invention that includes distal and proximal anchors.
Figure 6:
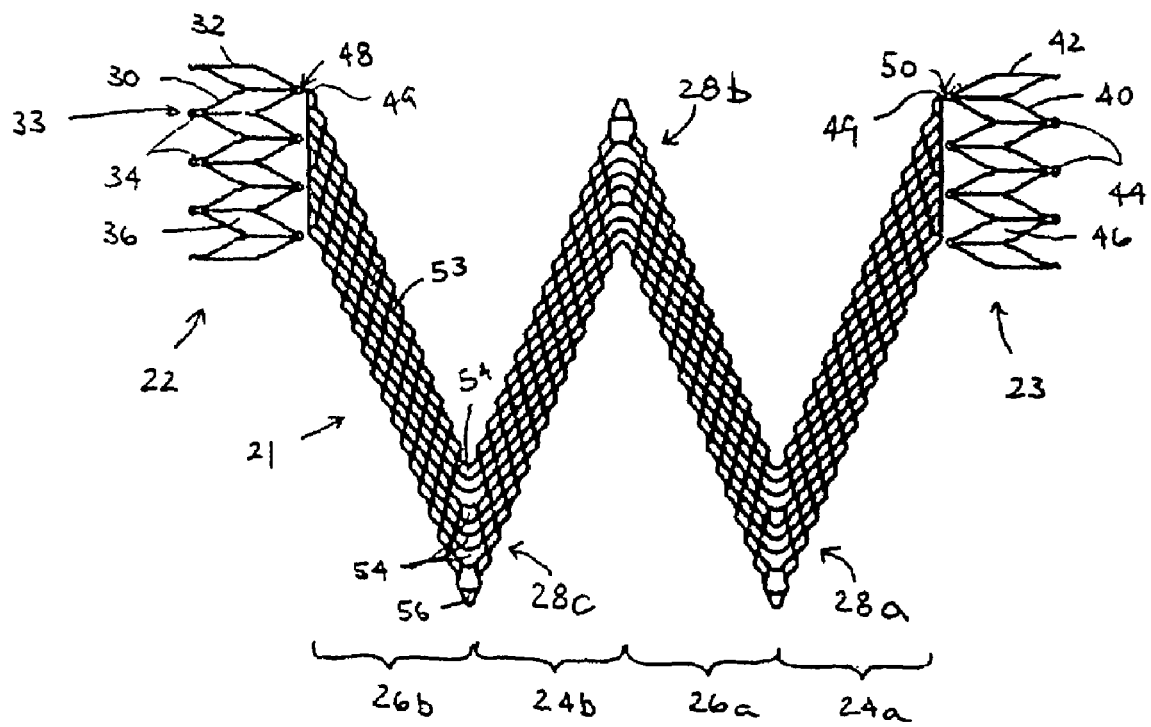
FIG. 6 is a schematic representation of the vascular prosthesis of FIG. 5 shown in a flattened configuration.

Referring to FIGS. 5 and 6, another embodiment of vascular prosthesis 20 is shown, which includes optional distal and proximal anchor sections 22, 23. Distal anchor section 22 preferably is a tubular mesh structure that is coupled to a distal end of alternating helical section 21. In particular, distal anchor section 22 includes a pair of concentrically aligned zig-zag rings 30 that are spaced from one another and coupled by struts 32. Struts 32 extend between corresponding apices 34 of rings 30 and are oriented parallel to a longitudinal axis of vascular prosthesis 20. Apices 34 may comprise one or more radiopaque markers 33 such as a radiopaque marker band or coating. As a result, rings 30 and struts 32 combine to define a plurality of openings 36 shaped as parallelograms, thereby forming a tubular mesh. The tubular mesh preferably is formed by laser cutting a solid tube.

Distal anchor section 22 preferably is formed from a solid tubular member comprising a shape memory material, such as nickel-titanium alloy, which is laser cut, using techniques that are known in the art, to a desired deployed configuration. Preferably, distal anchor section 22 is cut from the tube so that rings 30 and struts 32 are formed as a single monolithic body. However, it should be appreciated that distal anchor section 22 may be constructed from separate rings 30 and struts that are mechanically coupled in a secondary operation, such as by welding, soldering or employing a mechanical fastener, such as a rivet. An appropriate heat treatment then may be applied so that distal anchor section 22 may be configured to self-deploy radially outward from a contracted, delivery configuration to a deployed configuration in conjunction with alternating helical section 21, described above. Alternatively, distal anchor section 22 may be configured to be balloon expandable.

Proximal anchor section 23 also preferably has a tubular mesh construction. Proximal anchor section 23 includes a pair of concentrically aligned zig-zag rings 40 that are spaced from one another and coupled by struts 42. Struts 42 extend between corresponding apices 44. Apices 44 may comprise one or more radiopaque markers 43 such as a radiopaque marker, band or coating. Rings 40 are oriented parallel to longitudinal axis X of vascular prosthesis 20. Rings 40 and struts 42 combine to define a plurality of openings 46 shaped as parallelograms. Similar to distal anchor section 22, the tubular mesh structure of proximal anchor section 23 preferably is formed by laser cutting a solid tube. Proximal anchor section 23 may be constructed in the same manner described above with respect to distal anchor section 22. Alternatively, proximal anchor section 23 also may be constructed to be balloon expandable.

Moreover, distal anchor section 22 and proximal anchor section 23 may have different constructions. Although distal anchor section 22 and proximal anchor section 23 as described above are identical, they alternatively may have different zig-zag or cell structures or deployment modes (e.g., self-expanding at the distal end and balloon expandable at the proximal end). For example, anchor sections 22, 23 may be constructed as a single zig-zag ring. As a further alternative, anchor sections 22, 23 may be configured so that openings 36, 46 have shapes other than parallelograms, e.g., openings 36, 46 may be shaped as diamonds or any other polygonal shape, circles or ellipses. Furthermore, although anchor sections 22, 23 are illustrated as including struts 32, 42 extending between each set of corresponding apices, struts 32, 42 may extend between fewer sets of corresponding apices. For example, struts may extend between relatively few apices. In addition, the distance between the zig-zag rings of anchor sections 22, 23 may also be selected to provide an anchor section of any desired length.

Furthermore, the outer edges of anchor sections 22, 23 may be biased so that the proximal-most edge of anchor section 23 and the distal-most edge of anchor section 22 expand further radially outward than with respect to longitudinal axis X than the remainder of the anchor section. This configuration may be useful to increase radial outward force upon a patient's vessel and thus improve anchoring of vascular prosthesis 20 within the vessel. Such a biased configuration may be established by heat-treating a shape memory material using techniques that are known in the art.

Distal anchor section 22 is coupled to the distal end of alternating helical section 21 at junction 48. Similarly, proximal anchor section 23 is coupled to the proximal end of alternating helical section 21 at junction 50. Preferably, junctions 48, 50 are formed from a strut of alternating helical section 21 that extends from that section and is coupled to a portion of the adjacent zig-zag rings 30, 40 of the respective anchor section 22, 23.

Junctions 48, 50 may comprise one or more radiopaque markers 52 such as a radiopaque marker band or coating. Radiopaque marker 52 facilitates positioning of junctions 48, 50 at a desired longitudinal position within a patient's vessel, and further facilitates alignment of vascular prosthesis 20 at a desired axial orientation within the vessel. For example, radiopaque markers 52 may be used to orient alternating helical section 21 so that a desired lateral surface of alternating helical section 21 deploys to overlay the diseased vessel segment.

It will be apparent to those skilled in the art that junctions 48, 50 may comprise other strut arrangements to connect distal anchor section 22 and proximal anchor section 23 to alternating helical section 21. For example, more than one strut may extend from alternating helical section 21 to a respective anchor 22, 23.

Various alternate junction configurations will be described which may be used to couple distal anchor section 22 and/or proximal anchor section 23 to alternating helical section 21.

As described above and as shown in FIGS. 5 and 6, anchors 22, 23 are preferably coupled to alternating helical section 21 by one or more struts 49 that extend generally parallel to longitudinal axis X of the vascular prosthesis. Struts 49 may be any desired length and may extend to any portion of the adjacent anchor. For example, struts 49 may extend to an apex 34 of anchor 22 or any other portion of anchor 22. In addition, struts 49 may extend from any portion of alternating helical section 21 near an end of the section. For example, as shown in FIG. 6, strut 49 extends from a tip of alternating helical section 21. Alternatively, struts 49 may extend from a portion of alternating helical section 21 away from the tip.

In one preferred embodiment, alternating helical section 21, distal anchor section 22 and proximal anchor section 23 are integrally formed as a single monolithic body, such as by laser cutting all three components from a single tube. In such a construction of vascular prosthesis 20, the struts extending from alternating helical section 21 that form junctions 48, 50 also may form struts 32, 42 of the respective anchor section 22, 23. Alternatively, anchor sections 22, 23 may be manufactured separately from alternating helical section 21 and mechanically coupled in a subsequent process, such as by soldering, welding, installing mechanical fasteners (e.g., rivets) or other means, as will be apparent to one skilled in the art.

In operation, the overlap of portions of the alternating helical section when it is in the contracted state and the number of helical portions, causes alternating helical section 101 to deploy in a unique sequence, as will be described in greater detail below with reference to FIGS. 8A-8D. Advantageously, the order of deployment of the portions of alternating helical section 71 alleviates drawbacks associated with the prior art such as the tendency of the turns of the helical section to jump or shift during deployment and also results in the location of deployment being more easily controlled. Another benefit is that deployment of discrete segments may be more easily controlled. Additionally, the alternating helical section may be balloon expandable, in particular, the structure allows a user to post dilate discrete sections with a balloon. For example, a user may expand a selected portion of the device adjacent a specific apex.

Figure 7:
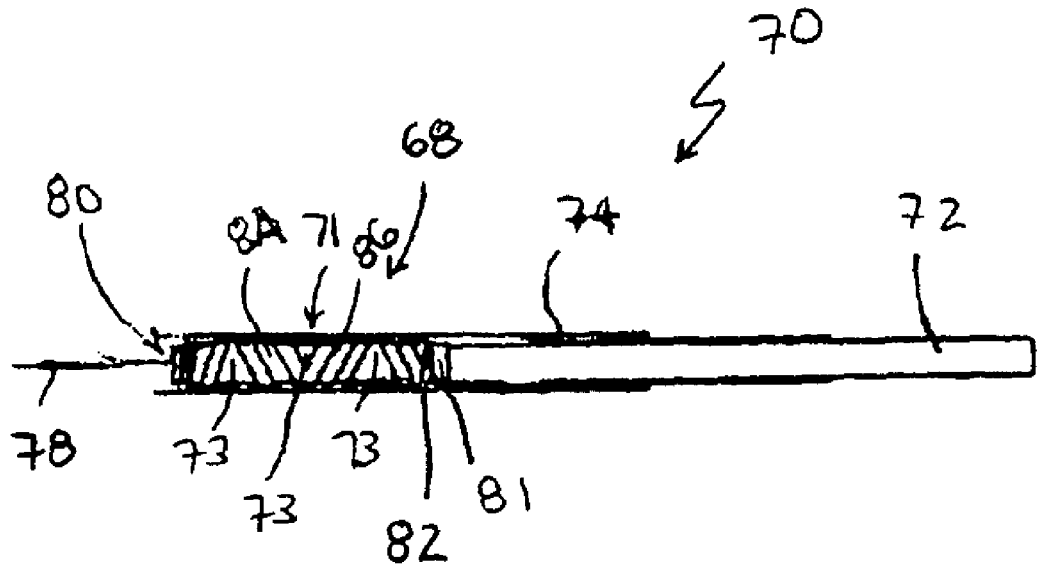
FIG. 7 is a cross-sectional view of a delivery system suitable for use in delivering the vascular prosthesis of FIG. 3.

In FIG. 7, a general delivery system 70 suitable for use in delivering a vascular prosthesis of the present invention is described. Delivery system 70 comprises catheter body 72, which is generally an elongate body, and outer sheath 74. Catheter body 72 may also include a lumen dimensioned for the passage of guidewire 78. Catheter body 72 preferably includes distal marker 81 and stop 80 located adjacent the distal end of alternating helical section 71 and proximal stop 82 located adjacent the proximal end of alternating helical section 71.

Distal stop 80 may comprise a raised ledge on catheter body 72 so that the distal end of alternating helical section 71 bears on the ledge to prevent relative movement between alternating helical section 71 and catheter body 72 in the distal direction. Alternatively, distal stop 80 may comprise a plurality of raised pins or knobs that prevent relative motion between alternating helical section 71 and catheter body 72 parallel to the longitudinal axis. Proximal stop 82 also may comprise a raised ledge, pins or knobs on catheter body 72, and both distal and proximal stops 80 and 82 may be radioopaque, so as to be visible under a fluoroscope and provide a radiopaque marker.

Vascular prosthesis 68 is collapsed onto catheter body 72 by winding alternating helical section 71 around catheter body 72. In order to wind alternating helical section 71 on catheter body 72, inner apices 73a and 73c may be temporarily coupled to catheter body 72 and the remainder of alternating helical section 71 is wound around catheter body 72 until it is collapsed as shown in FIG. 7. Alternating helical section 71 is wrapped so that the distal and proximal ends and outer apex 73b are located radially outward from the remainder of the alternating helical section 71.

After alternating helical section 71 is wound on catheter body 72, outer sheath 74 is advanced distally over catheter body 72 to capture alternating helical section 71 between catheter body 72 and outer sheath 74.

Figure 8A:
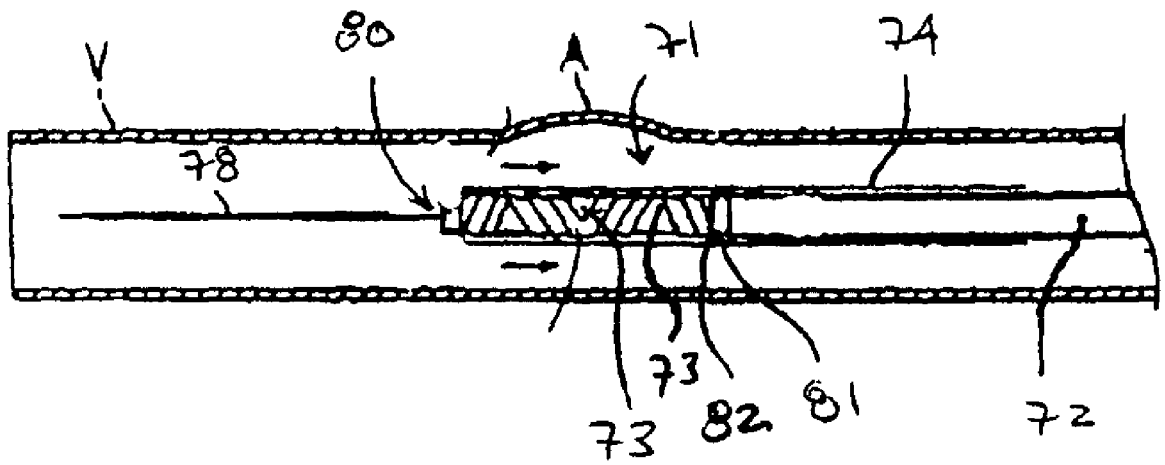
FIGS. 8A-8D are side sectional views illustrating use of the vascular prosthesis in the treatment of an aneurysm.

Referring to FIG. 8A, in operation, guidewire 78 is percutaneously and transluminally advanced through a patient's vasculature, using techniques that are known in the art. Guidewire 78 is advanced until a distal end of guidewire 78 is positioned distal of aneurysm A, which is situated in vessel V. Delivery system 70, having vascular prosthesis 68 contracted therein, then is advanced over guidewire 78 via the central lumen of catheter body 72. Delivery system 70 preferably is advanced under fluoroscopic guidance until distal marker 81 is situated distally to aneurysm A and alternating helical section 71 and apex 73b are situated adjacent to the aneurysm.

Once alternating helical section 71 is located adjacent to aneurysm A, outer sheath 74 is retracted proximally to cause alternating helical sections to deploy sequentially until outer sheath 74 is retracted to proximal stop 82.

Figure 8B:
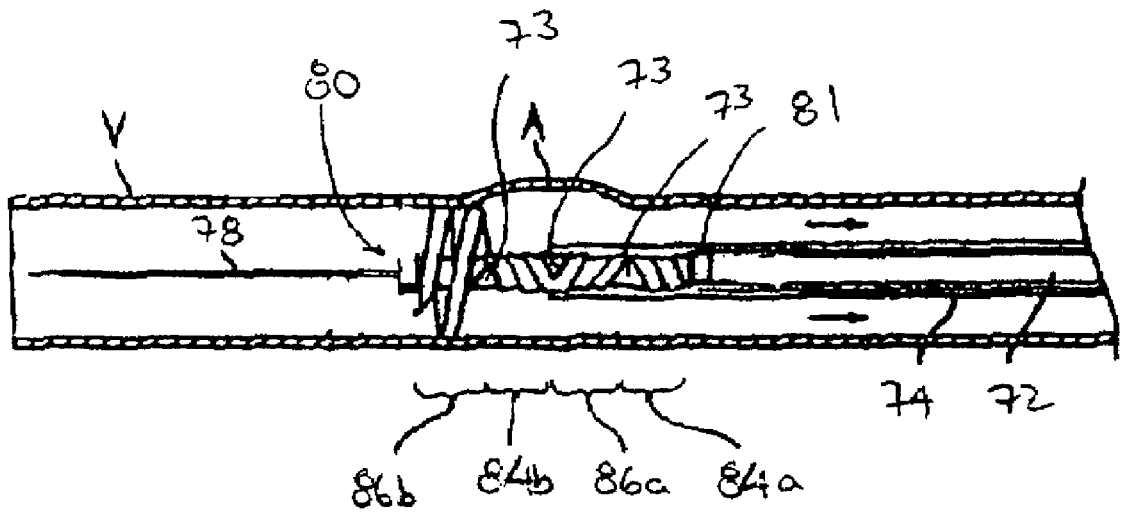
Figure 8C:
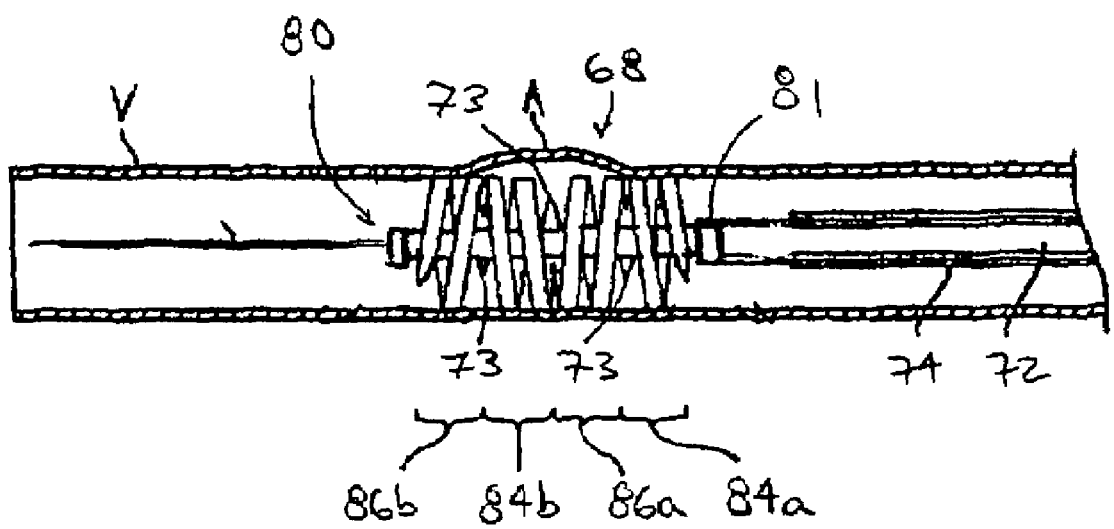

Referring to FIGS. 8B and 8C, after the distal end of alternating helical section 71 is secured distal of aneurysm A, outer sheath 74 is further retracted proximally to allow alternating helical section 71 to continue to expand and deploy to its predetermined deployed shape. Because central portions of the alternating helical section are over-wrapped, rotation of catheter body 102 is not required for the alternating helical section to expand.

As outer sheath 74 is further retracted, the turns of alternating helical section 71 unwind in a unique and controlled manner and engages and conforms to an inner wall of vessel V in a controlled manner. Helical portion 86b expands as outer sheath 74 is moved proximal of the distal end of alternating helical section 71. Helical portion 86b is capable of expanding because the distal end of alternating helical section 71 is outwardly wrapped so there is no overlap of an adjacent portion retaining it in the contracted state. Helical portion 84b may not be able to fully expand until the distal end of outer sheath 74 is moved proximal of apex 73b because, in the present embodiment, alternating helical section 71 is wound so that apex 73b is located radially outward (i.e., outer-wrapped) and, as a result, each turn of helical portion 84b overlaps the adjacent distal turn of that portion. After the distal end of outer sheath 74 is moved proximal of apex 73b, helical portions 84b and 86a are allowed to expand. Finally, after sheath 74 is moved proximal of the proximal end of alternating helical section 71, helical portion 84a is able to expand, as illustrated in FIG. 8C. It will be appreciated that due to this construction, portions of alternating helical section 71 are capable of expanding independent of other portions of alternating helical section.

Proximal movement of outer sheath 74 may be halted once the distal edge of outer sheath 74 is substantially aligned with proximal stop 82 to allow alternating helical section 71 to expand. It will be appreciated that because of the sequence of deployment of alternating helical section 71, the location of the deployed alternating helical section 71 may be easily controlled and the problems encountered in previous systems (e.g., stent jumping) may be avoided.

Figure 8D:
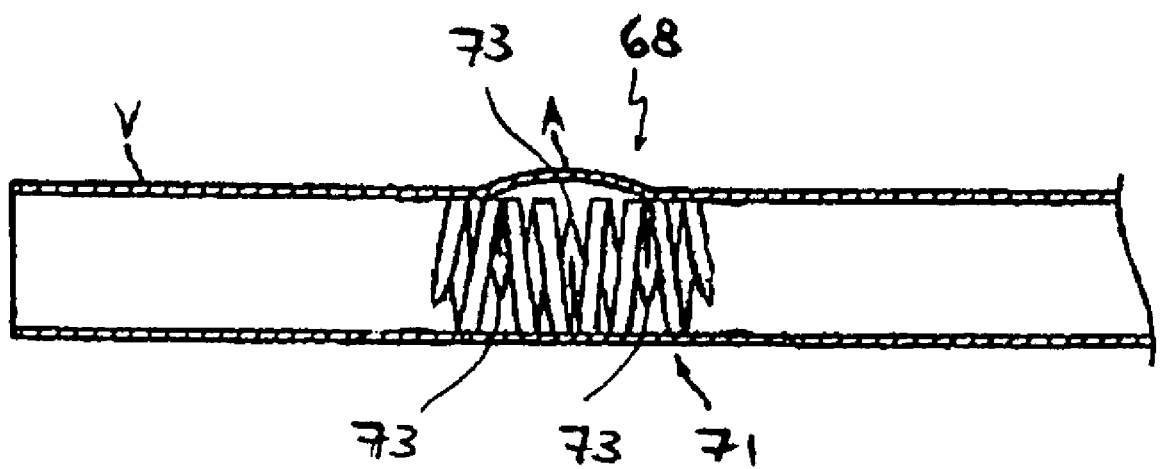

When vascular prosthesis 68 is fully deployed, delivery system 70 is proximally retracted over guidewire 78 and withdrawn from the patient's vessel, and guidewire 78 is removed. After removal of delivery system 70 and guidewire 78, vascular prosthesis 68 remains deployed, as shown in FIG. 8D.

Figure 9:
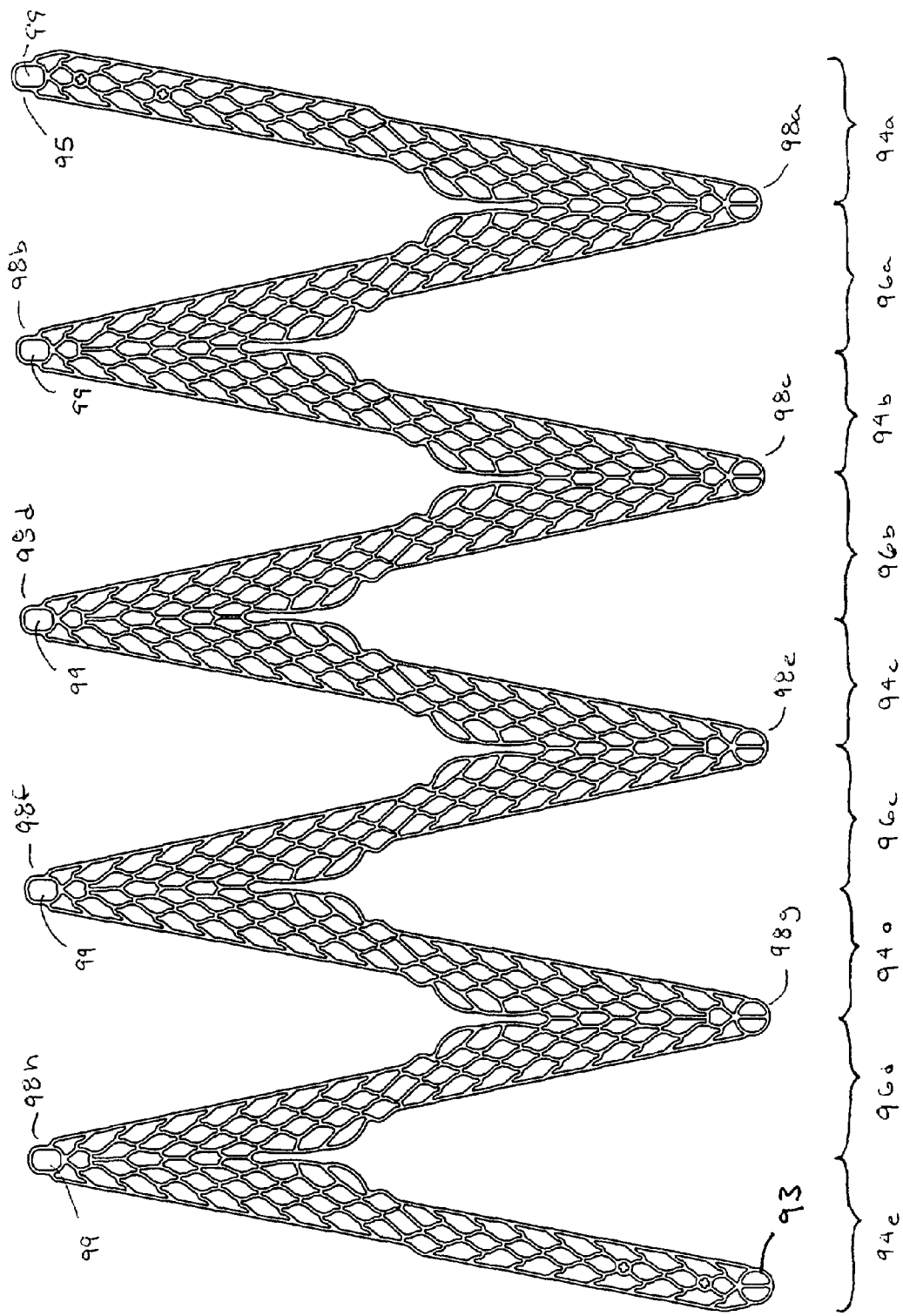
FIG. 9 is a schematic representation of a vascular prosthesis shown in a flattened configuration.

Referring to FIGS. 9-11, vascular prosthesis 90 and a corresponding delivery system 100 will be described. Vascular prosthesis 90 is constructed from alternating helical section 91 which includes a plurality of helical portions 94, 96 that are joined by apices 98. Alternating helical section 91 includes tip 95 at a proximal-most end that is configured to be inner wound. Helical portion 94a extends from tip 95 to apex 98a where it is coupled to a proximal end of helical portion 96a. Helical portion 96a extends between apices 98a and 98b and is coupled to a proximal end of helical portion 94b. That structure repeats through alternating helical section 91, as shown, and ends at a distal tail 93 that is configured to be outer wound. Proximal tip 95 and apices 98b, 98d, 98f and 98h are configured to be inner wound and each is designed to complement retainer 101 so that they may be temporarily coupled to catheter body 102 at least during loading of vascular prosthesis 90 into delivery system 100.

Delivery system 100 is particularly well-suited for delivering and deploying vascular prosthesis 90. Delivery system 100 generally includes catheter body 102, a plurality of retainers 101 and outer sheath 104. Catheter body 102 is generally an elongate tubular body that defines lumen 106 that is configured to receive guidewire 108. Catheter body 102 may be configured to have a generally constant outer diameter or the outer surface of catheter may be contoured such that the outer diameter varies over the length. Catheter body 102 also includes an optional proximal stop 107 that provides a shoulder to prevent proximal translation of vascular prosthesis 90 on catheter body 102. One or more radiopaque markers 109 may also be included on catheter body 102 to assist in placement of vascular prosthesis in a vessel. It should be appreciated that the elongate tubular body may have any configuration such as a multi-lumen configuration so that separate lumens are provided for guidewire and a retaining wire if desired. It should also be appreciated that the stop is an optional feature that may be omitted if desired for a selected prosthesis.

Additionally, the effective outer diameter of catheter body 102 may be altered by pads 105 that extend radially outward from the outer surface of catheter body 102. Pads 105 may be resilient rings that are coupled to the outer surface of catheter body 102 and spaced from retainers 101. Catheter body is preferably constructed from a resilient material such as nylon, so that it is flexible. Pads 105 may be made from any rigid or resilient material. Preferably, pads are constructed from urethane.

Retainers 101 are configured to couple inner wound proximal tip 95 and apices 98b, 98d, 98f and 98h to catheter body 102 during loading. In the present embodiment, retainers 101 are eyelets. Each retainer includes tab 110 that is defined by a pair of recesses 111, or notches, in catheter body 102. As a further alternative, and as described below with regard to additional embodiments, the retainer may include a single notch or indentation. Each tab 110 has a size and shape that complements the tip openings defined by proximal tip 95 and apices 98b, 98d, 98f and 98h so that tab 110 may be received therein. Retaining wire lumen 112 extends longitudinally through catheter body 102 and each of tabs 110. Retaining wire lumen 112 is located so that space 116 is created between retaining wire 114 and the surface of recesses 111. It should be appreciated that the retainers may alternatively or additionally be formed as grooves, hooks or any other feature that is capable of retaining a portion of a prosthesis as desired.

In the present embodiment, retaining wire 114 extends over struts that define tip openings of the prosthesis. However, as will be apparent from the additional embodiments described below, the retaining wire may be interlaced through portions of the prosthesis. For example, the retaining wire may extend through the tip openings. The retaining wire is preferably constructed from a low friction material. Additionally, the retaining wire may be constructed from a stretchable material so that when it is stretched the diameter reduces thereby easing removal. As a further alternative, the retaining wire may be constructed from Nitinol so that electrical current may be applied to reduce the diameter to ease removal. As a further alternative, the retaining wire may be constructed from a material that dissolves in response to exposure to a lytic material or blood. As a still further alternative, the retaining wire may be configured to dissolve in response to an application of electrical current.

Support members 103 may also be included. Support members 103 are generally semi-rigid member that are molded into catheter body 102 adjacent the openings of retaining wire lumen 112. Support members 103 are included to provide support to the relatively soft material that is used to construct catheter body 102 in locations having reduced thickness. Preferably, a plurality of spaced support members 103 are employed so that the flexibility of catheter body 102 is not significantly reduced.

Referring to FIG. 11, an exemplary retainer 101 of delivery system 100 is shown with a inner wound apex 98 coupled thereto. The dimensions of space 116 are selected so that the retained portion of vascular prosthesis 90 may be received therein.

Vascular prosthesis 90 is loaded into delivery system 100 by first aligning proximal tip 95 and apices 98b, 98d, 98f and 98h with respective retainers 101 and engaging tabs 110 with openings 99 so that portions of vascular prosthesis 90 are received in recesses 111. Next, retaining wire 114 is extended through lumen 112 so that it overlays the portions of vascular prosthesis 90 received in recesses 111 and retains those portions therein. Catheter body 102 is rotated relative to outer wound apices 98a, 98c, 98e and 98g, and distal tail 93 until helical portions 94, 96 are wound down so that they at least partially overlap themselves and the inner wound apices 98 and proximal tip 95. After alternating helical section 91 is wound down, outer sheath 104 is extended over catheter body 102 and vascular prosthesis 90 to retain the outer wound apices 98 and distal tail 93 in that contracted state. It should be understood that in the present embodiment proximal tip 95 is located adjacent proximal stop 107 of catheter body 102 so that during deployment retraction of outer sheath 104 does not cause vascular prosthesis 90 to translate on catheter body 102. It should be appreciated that the prosthesis may also be wrapped more tightly upon the catheter body to prevent it from translating.

After outer sheath 104 is advanced over catheter body 102 and vascular prosthesis 90, retaining wire 114 preferably is retracted and removed from delivery system 100. It should be appreciated that retaining wire 114 may be retracted and removed during the manufacturing of the system after winding the stent down or after outer sheath 104 is disposed over the catheter body and vascular prosthesis. Alternatively, retaining wire 114 may be retracted and removed during stent deployment. For example, the retaining wire may be attached to the outer sheath and configured to release the stent immediately before the outer sheath is retracted to expose the prosthesis. The prosthesis may alternatively be released separately at the same time as the sheath is retracted or following the retraction of the outer sheath.

Figure 12:
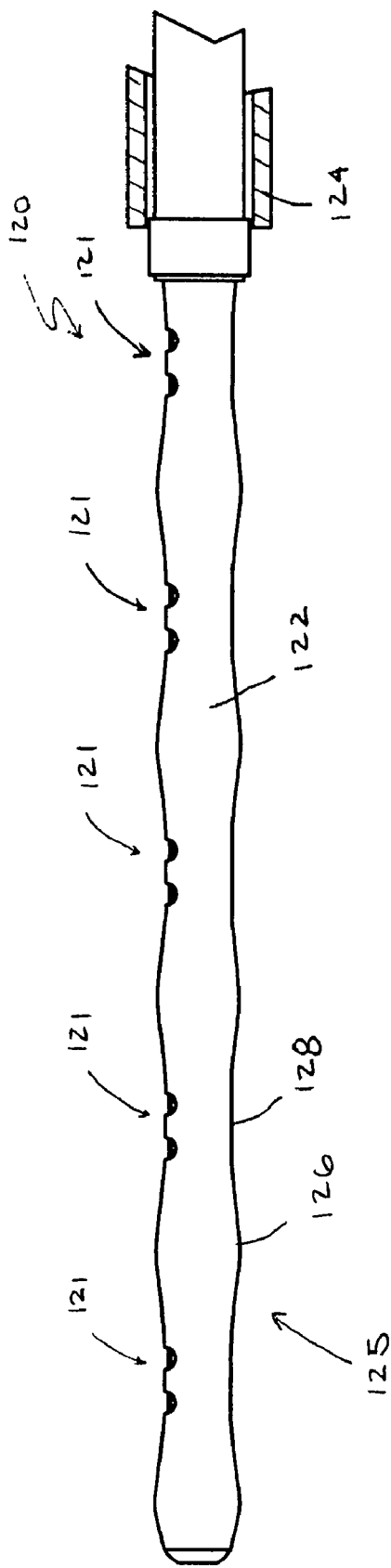
FIG. 12 is a side view of another delivery device suitable for delivering a stent having an alternating helical section.

Referring now to FIG. 12 an alternative embodiment of the delivery system will be described. Delivery system 120 generally includes catheter body 122, a plurality of retainers 121 and outer sheath 124. Catheter body 122 is generally an elongate tubular body that defines a guidewire lumen. Catheter body 122 has an outer diameter that varies over its length so that the outer surface has an undulating contour that defines a plurality of peaks 126 and valleys 128. The outer diameter varies such that peaks 126 are generally located midway between adjacent retainers 121. In addition, peaks 126 generally have an identical diameter and valleys 128 generally have an identical diameter. It should be appreciated that undulations 125 may be located so that retainers 121 are generally located at any location along the undulating contour. For example, retainers 121 may alternatively be located at peaks 126 of undulations 125 rather than at valleys 128 as shown. The specific structures of retainers 121 and outer sheath 124 are substantially identical to the components described above with respect to the previous embodiment.

Figure 13:
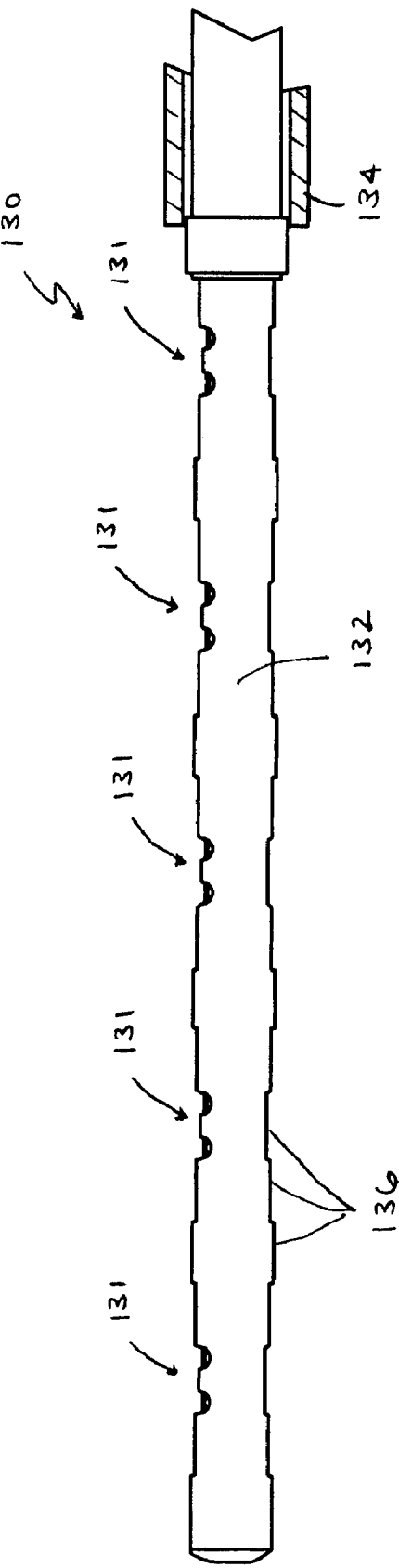
FIG. 13 is a side view of another delivery device suitable for delivering a stent having an alternating helical section.

Referring to FIG. 13, a further embodiment, delivery system 130, will be described. Delivery system 130 generally includes catheter body 132, retainers 131 and outer sheath 134. Catheter body 132 has a structure that is similar to the previous embodiment, in that it includes an outer diameter that varies over its length. In particular, catheter body 134 includes an outer contour that includes a plurality of steps 136 and retainers 131 are included at steps 136 where the outer diameter is the smallest. It should be appreciated, however, that the steps may be located so that retainers 131 are located at any location among steps 136. The specific structures of retainers 131 and outer sheath 134 are substantially identical to the components described above.

Figure 14:
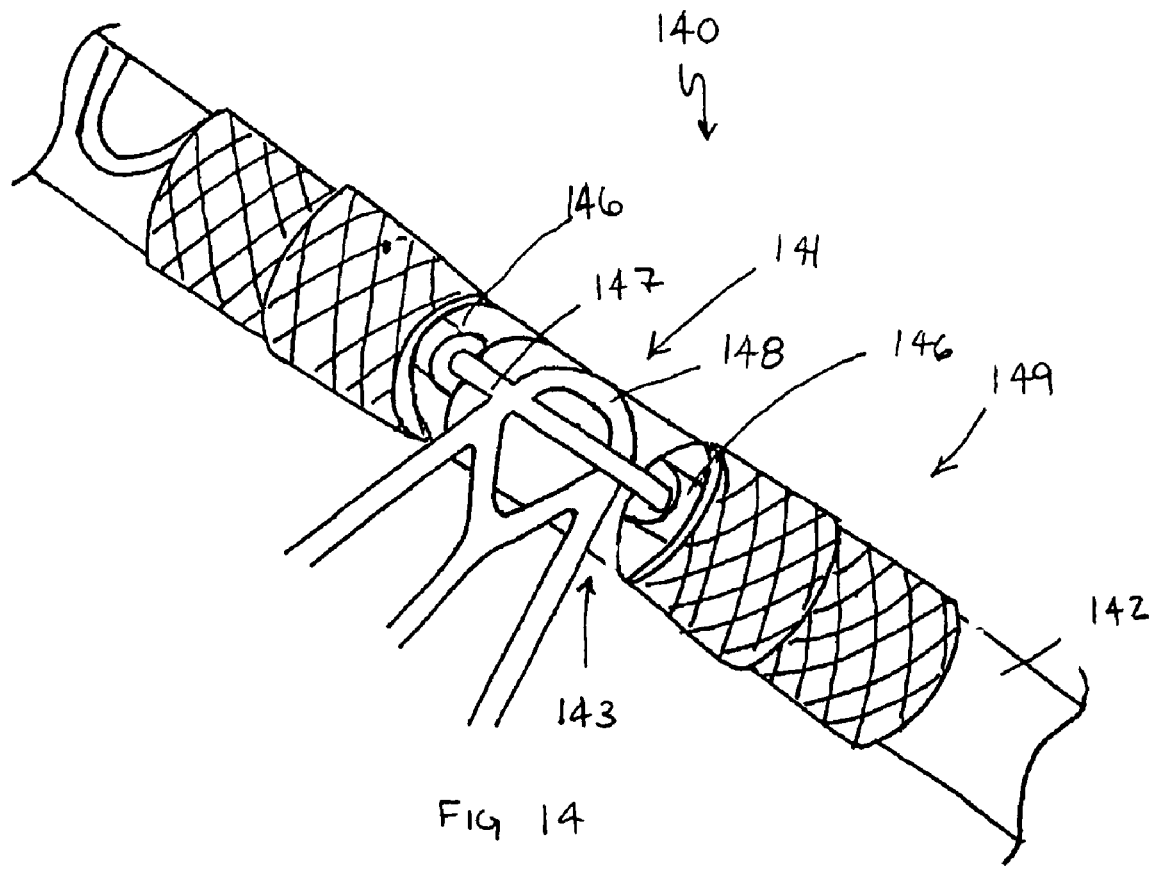
FIG. 14 is a perspective view of a retainer portion of another delivery device suitable for delivering a stent having an alternating helical section.
Figure 15:
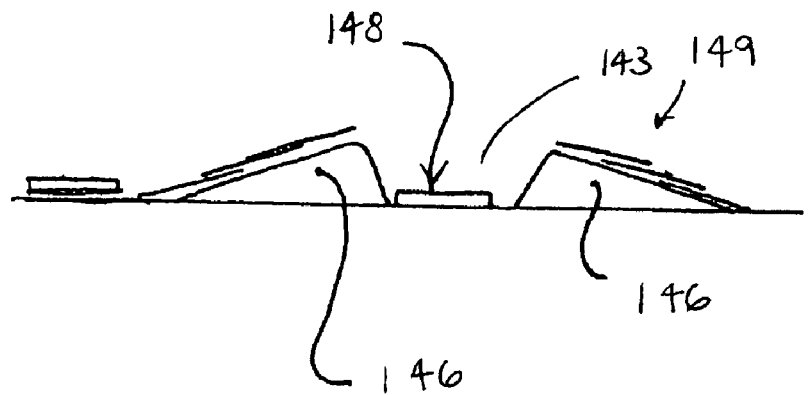
FIG. 15 is a side cross-sectional view of the retainer portion of FIG. 14.

Referring to FIGS. 14 and 15 additional surface features that may be included on catheter body 142 of delivery system 140 will be described. In particular, catheter body 142 includes ramps 146 that extend from the outer surface of catheter body 142. Ramps 146 also generally create one large recess 143 that forms a part of retainer 141. An inner wound apex 148 of vascular prosthesis 149 is received in recess 143, between ramps 146, and retaining wire 147 extends over apex 148 across recess 143. Alternatively, the retaining wire may extend through the apex. Adjacent helical portions of vascular prosthesis 149 are wound around catheter body 142 and wedges 146. Although ramps are illustrated, it should be appreciated that any shaped feature may be included such as a square groove.

It will be appreciated that catheter bodies 122 and 132 may be constructed from any material desired. In addition, multiple materials may be used to provide resilient and rigid portions or varying resilience over the length of the body.

The shape, size, position relative to the vascular prosthesis, and resiliency of pads 105, undulations 125, steps 136 and wedges 146 may be selected so that a vascular prosthesis loaded thereon is prevented from migrating along the catheter body during retraction of the outer sheath. For example, the features may be configured to act as stops that prevent relative longitudinal motion between the vascular prosthesis and the catheter body or the features may be configured so that contacting surface area between the vascular prosthesis and the outer sheath may be reduced.

Figure 16:
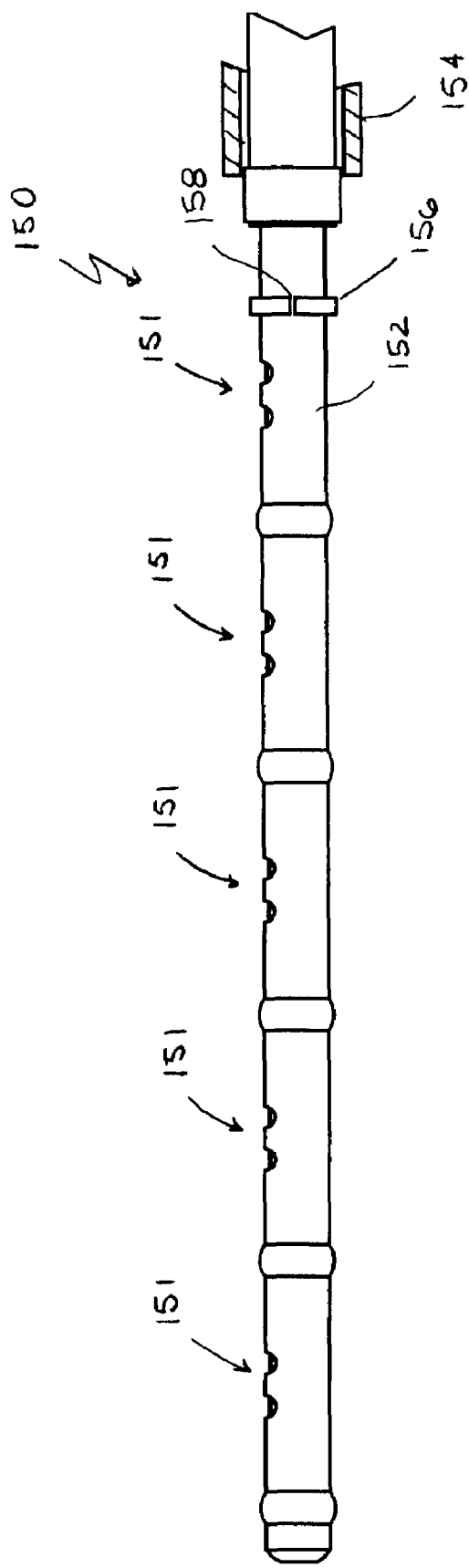
FIG. 16 is a side view of another delivery device suitable for delivering a stent having an alternating helical section and an anchor.
Figure 17:
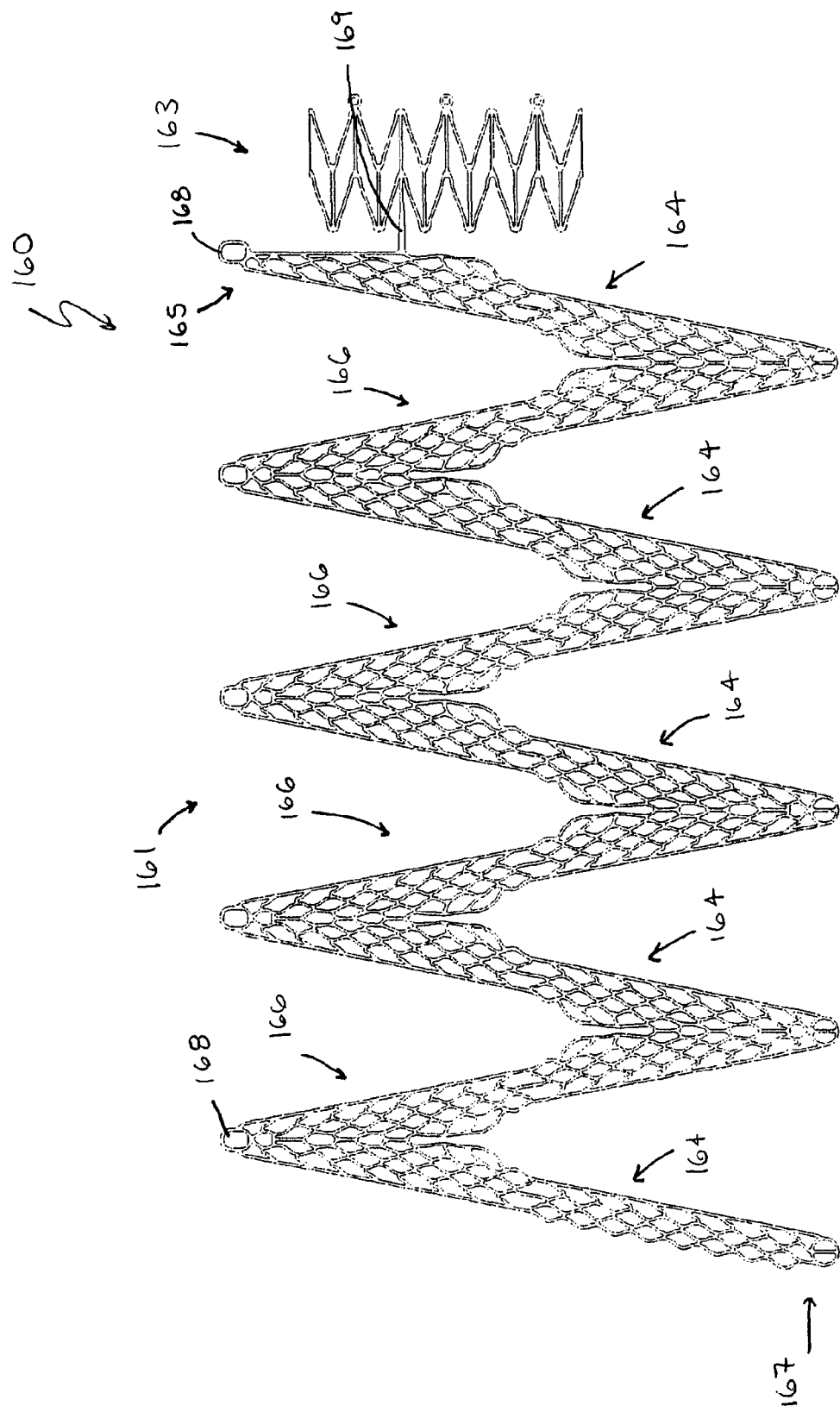
FIG. 17 is a schematic representation of a vascular prosthesis shown in a flattened configuration.

Referring to FIGS. 16 and 17, delivery system 150 for vascular prosthesis 160 will be described. Delivery system 150 is particularly well-suited to delivery of a vascular prosthesis having a single proximal anchor, such as that shown in FIG. 17. Vascular prosthesis 160 includes alternating helical section 161 and anchor 163 that is coupled to a proximal end of alternating helical section 161. Alternating helical section includes a plurality of helical portions 164, 166 that are joined by apices 168. Alternating helical section 161 includes tip 165 at a proximal-most end that is configured to be inner wound and a tail 167 at a distal-most end that is configured to be outer wound. Anchor 163 is coupled to alternating helical section 161 by junction 169, which is a strut that extends generally longitudinally between alternating helical section 161.

Delivery system 150 includes catheter body 152, retainers 151 and outer sheath 154 which are generally identical to those previously described in relation to other embodiments. Delivery system 150 includes at least one intermediate stop 156 that is located on catheter body 152 so that it is between alternating helical section 161 and anchor 163 when vascular prosthesis 160 is in a contracted delivery state within delivery system 150. Intermediate stop 156 is generally annular and includes a channel 158 that is configured to receive junction 169 when vascular prosthesis 160 is in the contracted, delivery state. The intermediate stop prevents alternating helical section 161 from migrating toward anchor 163 during deployment.

Figure 18:
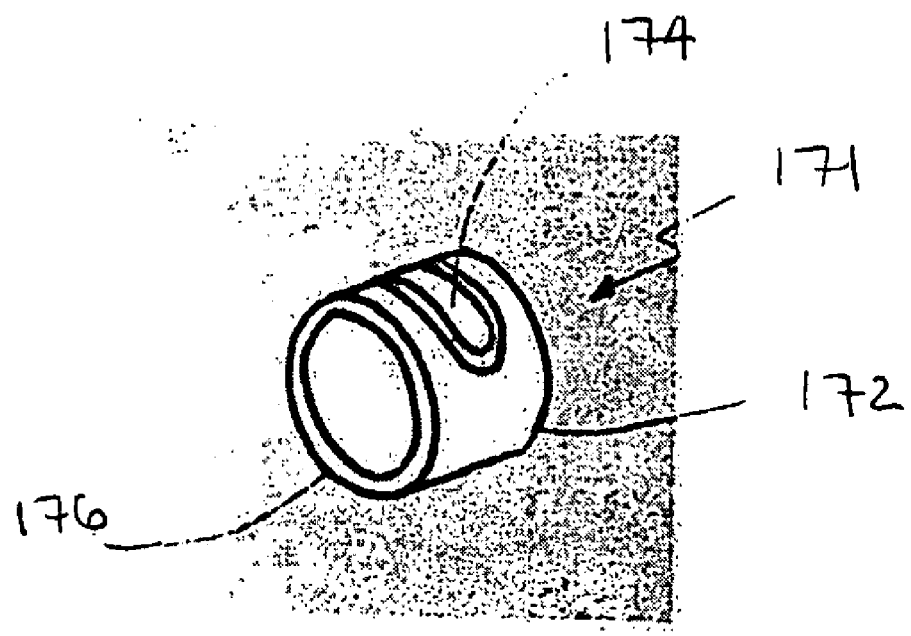
FIG. 18 is a perspective view of a retaining member suitable for a delivery device.
Figure 19:
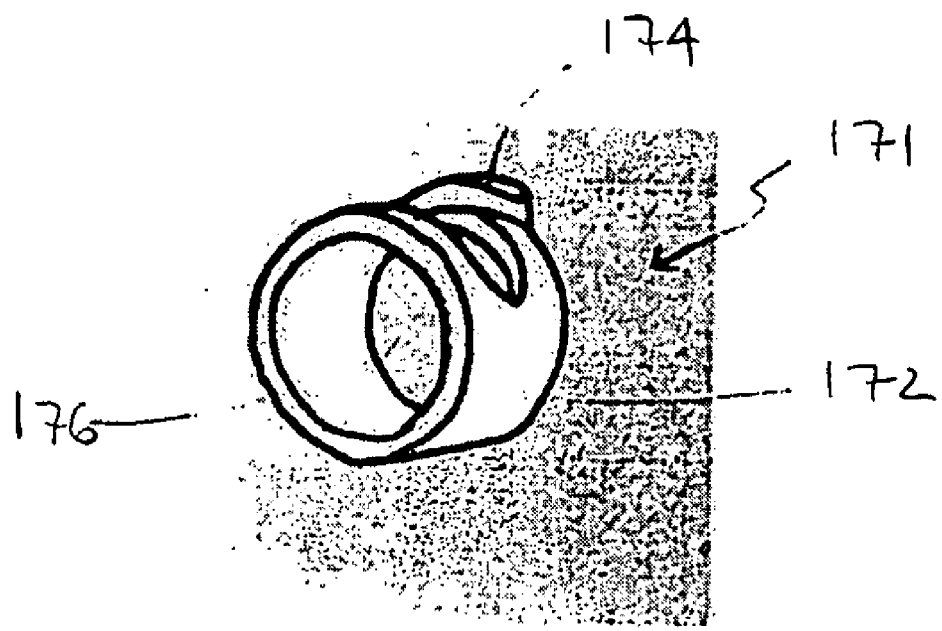
FIG. 19 is a perspective view of the retaining member of FIG. 18 in a loading configuration.

Referring to FIGS. 18 and 19, a retainer 171 that may be utilized in a delivery system will be described. Retainer 171 generally includes a tubular body member 172 defining a central lumen 176 that is configured to receive a catheter body of a delivery system and a flexible tab 174 that is able to be flexed from an at rest position, shown in FIG. 18, to a loading position, shown in FIG. 19. In the loading position, tab 174 is lifted so that an inner wound apex of a vascular prosthesis may be inserted and retained between tab 174 and body member 172. A low magnitude retaining force is exerted on the apex so that it remains retained during loading of the vascular prosthesis but is easily released after loading or during deployment of the vascular prosthesis, for example by rotating the catheter body relative to the prosthesis. Such retainers may be constructed from a shape memory material such as Nitinol. It should be appreciated that a material having thermal shape memory may be used so that a temperature change may cause the retainer to release the vascular prosthesis.

Figure 20:
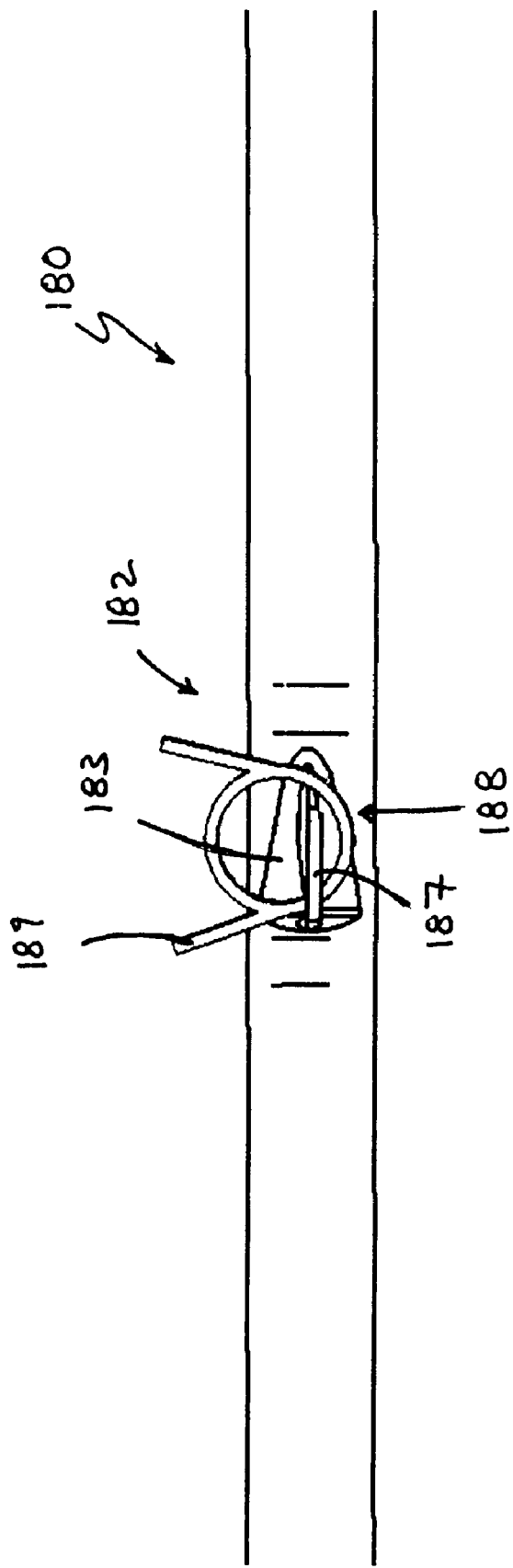
FIG. 20 is a top view of a retainer portion of another delivery device suitable for delivering a stent having an alternating helical section.
Figure 21:
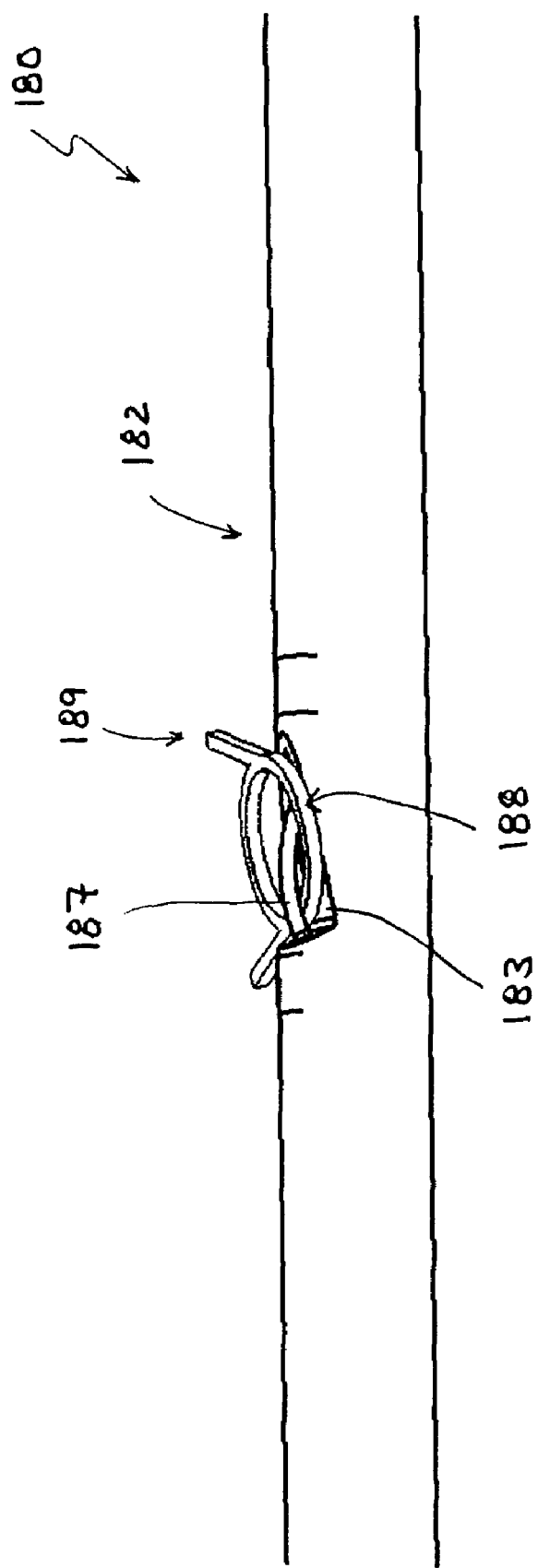
FIG. 21 is a perspective view of the retaining member of FIG. 20.

Referring now to FIGS. 20 and 21 additional surface features that may be included on catheter body 182 of delivery system 180 will be described. Catheter body 182 includes a plurality of indentations 183. An inner wound apex 188 of vascular prosthesis 189 is received in recess 183 and retaining wire 187 is laced through the opening at apex 188.

Figure 22:
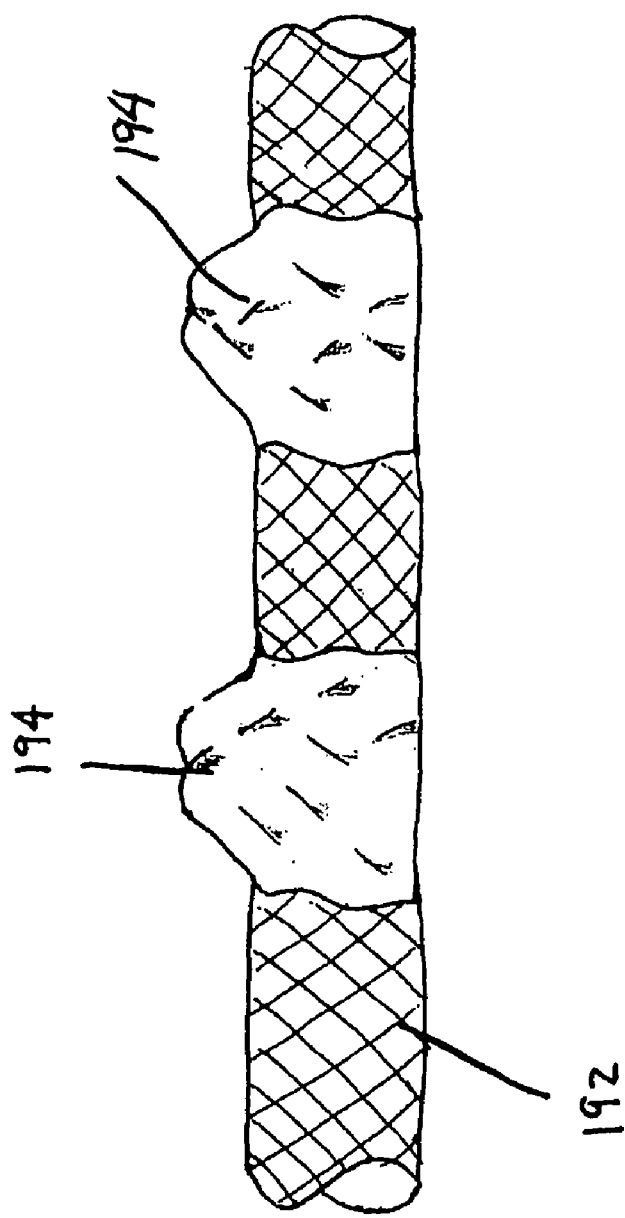
FIG. 22 is a side view of a retainer portion of another delivery device suitable for delivering a stent having an alternating helical section.
Figure 23:
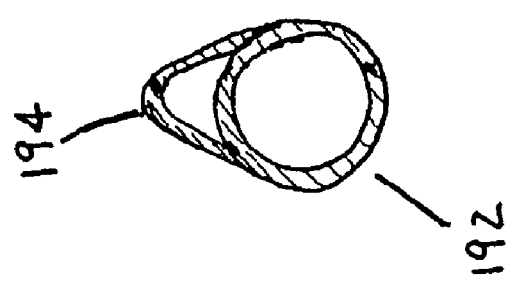
FIG. 23 is a cross-sectional view of the retaining member of FIG. 22.

Referring to FIGS. 22 and 23, another embodiment of surface features that may be included on catheter body 192 will be described. In the present embodiment, catheter body 192 is a braided shaft. Strands of the braided shaft are deformed so that they extend radially outward from the remainder of the braided shaft. After the strands are deformed, they may be soldered in the deformed position. The combination of the deformed strands and the solder forms a loop 194, as shown in FIG. 23, that may receive a retaining wire. In such an embodiment, the retaining wire need not extend through the catheter body but instead may extend along the outer surface of the catheter body and through loops 194.

Figure 24:
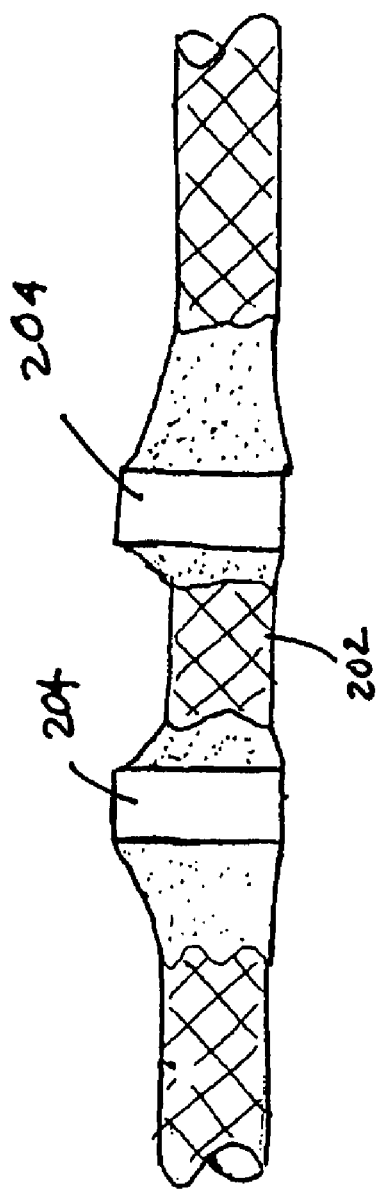
FIG. 24 is a side view of a retainer portion of another delivery device suitable for delivering a stent having an alternating helical section.
Figure 25:
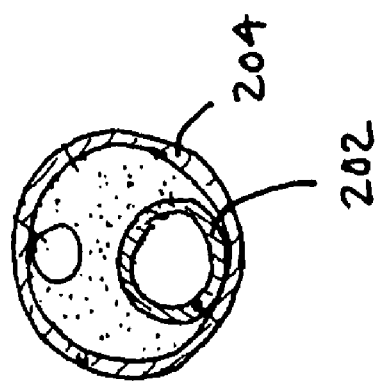
FIG. 25 is a cross-sectional view of the retaining member of FIG. 24.

In a still further embodiment, shown in FIGS. 24 and 25. Similar to the previous embodiment, catheter body 202 is constructed from a braided shaft. A plurality of hoops 204 are soldered externally to catheter body 202 so that there is a gap between a portion of each hoop 204 and catheter body 202. The parts are soldered so that an aperture remains after the parts are coupled, as shown in FIG. 25, so that a retaining wire may be received therein. It should be appreciated that hoops 204 may be radiopaque marker bands if desired. Similar to the previous embodiment, the retaining wire may extend along the outer surface of the catheter body and through hoops 204.

It will be appreciated that the retainers included in the delivery device may be any structure or material sufficient to temporarily retain apices of a vascular prosthesis on a catheter body of a delivery system. For example, an adhesive such as a temperature sensitive adhesive may be utilized.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method of loading a vascular prosthesis into a delivery system, comprising:
   providing a vascular prosthesis comprising an alternating helical section that includes at least three helical portions having alternating directions of rotation, wherein the helical portions are coupled to adjacent helical portions at apices, the apices comprising alternating outer and inner apices, the outer and inner apices extending in different directions;
   providing a delivery system including an elongate body, a plurality of retainers and an outer sheath;
   coupling the inner apices to the elongate body with the retainers while leaving the outer apices uncoupled from the elongate body;
   winding the alternating helical section around elongate body to a contracted state by wrapping at least a plurality of the outer apices around the elongate body; and
   advancing the outer sheath over the elongate body to capture the alternating helical section between the elongate body and the outer sheath with the outer apices remaining uncoupled from the elongate body.

2. The method of loading a vascular prosthesis of claim 1, further comprising uncoupling the inner apices from the elongate body.

3. The method of loading a vascular prosthesis of claim 2, wherein coupling the plurality of inner apices to the elongate body comprises extending a retaining wire through a retaining wire lumen defined by the elongate body such that the retaining wire extends through portions of the inner apices of the vascular prosthesis received in recesses of the retainers.

4. The method of loading a vascular prosthesis of claim 3, wherein uncoupling the inner apices from the elongate body comprises removing the retaining wire from the retaining wire lumen of the elongate body.

5. The method of loading a vascular prosthesis of claim 1, wherein the vascular prosthesis further comprises a proximal anchor.

6. The method of loading a vascular prosthesis of claim 5, further comprising contracting the proximal anchor on the elongate body to a contracted state prior to advancing the outer sheath over the elongate body and the vascular prosthesis.

7. The method of loading a vascular prosthesis of claim 2, wherein the uncoupling step is carried out prior to use of the vascular prosthesis with the outer sheath positioned over the elongate body and the vascular prosthesis.

8. The method of loading a vascular prosthesis of claim 1, wherein the winding step comprises at least partially overlapping the outer apices over other portions of the alternating helical section.

9. The method of loading a vascular prosthesis of claim 1, wherein the winding step comprises rotating the elongate body.

10. A method of loading a vascular prosthesis into a delivery system, comprising:

obtaining a vascular prosthesis comprising an alternating helical section that includes an axially extending series of helical portions having alternating directions of rotation, wherein each helical portion has proximal and distal ends, the proximal and distal ends of adjacent helical portions joined to form inner apices and outer apices, the helical portions having a cross-sectional shape which is flattened in a radial direction;

coupling at least a plurality of the inner apices to an elongate body of a delivery system while leaving the outer apices uncoupled from the elongate body, the elongate body including retainers and the delivery system including an outer sheath, the inner and outer apices extending in different directions;

the coupling step comprising extending a retaining wire through a retaining wire lumen defined by the elongate body such that the retaining wire extends through portions of at least a plurality of the inner apices of the vascular prosthesis received in recesses of the retainers;

winding the alternating helical section around elongate body to a contracted state by rotating at least a plurality of the outer apices around the elongate body;

the winding step comprising at least partially overlapping the outer apices over other portions of the alternating helical section;

advancing the outer sheath over the elongate body to capture the alternating helical section between the elongate body and the outer sheath with the outer apices remaining uncoupled from the elongate body;

uncoupling the inner apices from the elongate body by removing the retaining wire from the retaining wire lumen of the elongate body; and the uncoupling step being carried out prior to use of the vascular prosthesis with the outer sheath positioned over the elongate body and the vascular prosthesis.

* * * * *